(12) United States Patent
Zahn et al.

(10) Patent No.: US 7,572,879 B2
(45) Date of Patent: *Aug. 11, 2009

(54) FLUORINATED ALKYL SUBSTITUTED-THIENO[3,4-B]THIOPHENE MONOMERS AND POLYMERS THEREFROM

(75) Inventors: Steffen Zahn, Pennsburg, PA (US); Gauri Sankar Lal, Whitehall, PA (US); William Franklin Burgoyne, Jr., Bethlehem, PA (US); Kristen Elaine Minnich, Germansville, PA (US); Andrew Francis Nordquist, Whtehall, PA (US); Lloyd Mahlon Robeson, Macungie, PA (US); Francis Joseph Waller, Allentown, PA (US)

(73) Assignee: Air Products and Chemicals, Inc., Allentown, PA (US)

( * ) Notice: Subject to any disclaimer, the term of this patent is extended or adjusted under 35 U.S.C. 154(b) by 638 days.

This patent is subject to a terminal disclaimer.

(21) Appl. No.: 11/418,317

(22) Filed: May 5, 2006

(65) Prior Publication Data

US 2006/0223977 A1    Oct. 5, 2006

Related U.S. Application Data

(63) Continuation-in-part of application No. 11/128,538, filed on May 13, 2005, now Pat. No. 7,432,340, and a continuation-in-part of application No. 10/958,068, filed on Oct. 4, 2004, now Pat. No. 7,118,692, and a continuation-in-part of application No. 10/193,598, filed on Jul. 11, 2002, now Pat. No. 7,071,289.

(51) Int. Cl.
    *C08G 73/24*    (2006.01)
    *C08G 75/00*    (2006.01)
    *C08F 4/80*     (2006.01)

(52) U.S. Cl. ............ 528/377; 528/373; 528/401; 528/486; 528/499; 528/503; 525/535; 524/82; 524/84

(58) Field of Classification Search ............ 528/377, 528/373, 401, 486, 499, 503; 525/535; 524/82, 524/84
    See application file for complete search history.

(56) References Cited

U.S. PATENT DOCUMENTS

| | | | |
|---|---|---|---|
| 4,639,328 A | 1/1987 | Krause et al. | |
| 4,910,645 A | 3/1990 | Jonas et al. | |
| 4,959,430 A | 9/1990 | Jonas et al. | |
| 6,585,914 B2 | 7/2003 | Marks et al. | |
| 6,645,401 B2 | 11/2003 | Giles et al. | |
| 6,676,857 B2 | 1/2004 | Heeney et al. | |
| 6,695,978 B2 | 2/2004 | Worrall et al. | |
| 6,709,808 B2 | 3/2004 | Lelental et al. | |
| 7,432,340 B2* | 10/2008 | Zahn et al. | 528/377 |
| 2003/0085381 A1 | 5/2003 | Worrall et al. | |
| 2004/0010115 A1 | 1/2004 | Sotzing | |
| 2004/0074779 A1 | 4/2004 | Sotzing | |
| 2005/0209419 A1 | 9/2005 | Zahn et al. | |

FOREIGN PATENT DOCUMENTS

| | | |
|---|---|---|
| EP | 0 203 438 A1 | 12/1986 |
| EP | 0144013 | 1/1989 |
| EP | 1 559 739 A1 | 8/2005 |
| EP | 1 642 896 A1 | 4/2006 |

OTHER PUBLICATIONS

Pomerantz et al "Poly (2-decylthieno(3,4-b) thiophene. A New Soluble Low-Bandgap Conducting Polymer", Synthetic Metals 84 (1997), p. 243-244.
Neef and Ferraris; "Synthesis and Electronic Properties of Poly(2-Phenylthieno(3,4-b)Thiophene): A New Low Band Gap Polymer", Chem. Mater. 1999, 11, p. 1957-1958.
Sung Y. Hong, et al; "Understanding the Conformational Stability and Electronic Structures of Modified Polymers Based on Polythiopene"; Micromolecules 1992; pp. 4652-4657.
Pomerantz, M., et al; "Poly(2-Decylthieno[3,4-b]Thiophene-4,6-diyl. A New Low Band Gap Conducting Polymer"; Macromolecules; 2001; 34; pp. 1817-1822.

* cited by examiner

*Primary Examiner*—Duc Truong
(74) *Attorney, Agent, or Firm*—Michael K. Boyer

(57) ABSTRACT

Partially and fully fluorinated alkyl substituted thienothiophene monomers (and polymers thereof) wherein the monomers are represented by the formula:

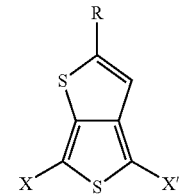

wherein
R is a partially or fully fluorinated primary, secondary or tertiary alkyl having from 1 to 8 carbon atoms; and
X and X' are independently selected from the group consisting of H, F, Cl, Br, I, MgCl,

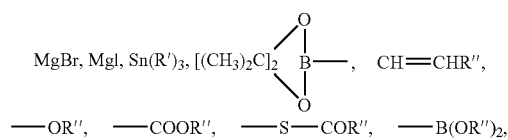

—COR", —C≡CH, and a polymerizable cyclic pi-conjugated carbon-ring structure optionally comprising S, N or O heteroatoms;
wherein
R' is a primary, secondary or tertiary alkyl having from 1 to 6 carbon atoms, and
R" is H or a primary, or tertiary alkyl having from 1 to 6 carbon atoms.

12 Claims, No Drawings

FLUORINATED ALKYL SUBSTITUTED-THIENO[3,4-*B*]THIOPHENE MONOMERS AND POLYMERS THEREFROM

CROSS-REFERENCE TO RELATED APPLICATIONS

This application is a CIP of Ser. No. 10/193,598 filed Jul. 11, 2002 now U.S. Pat. No. 7,071,289 And is a CIP of Ser. No. 10/958,068 filed Oct. 04, 2004 now U.S. Pat. No. 7,118,692 And is a CIP of Ser. No. 11/128,538 filed May 13, 2005 now U.S. Pat. No. 7,432,340

This application is related to U.S. patent application Ser. No. 10/193,598 entitled, Polymers Comprising thieno[3,4-b] Thienothiopnene and Methods of Making and Using the Same, filed on Jul. 11, 2002. application Ser. No. 10/193,598 is related to copending U.S. patent application Ser. No. 10/958,068 entitled, Substituted Thienothiophene Monomers and Conducting Polymers, filed on Oct. 4, 2004. The disclosure of these Applications is hereby incorporated by reference.

BACKGROUND OF THE INVENTION

Electrically conducting polymers are used in a variety of optoelectronics applications such as polymeric light emitting diodes for use in thin film displays, solid state lighting, organic photovolatics, advanced memory devices, organic field effect transistors, ultracapacitors and electroluminescent devices.

Polyacetylene was one of the first electrically conducting polymers to be extensively investigated and the discovery that polyacetylene exhibited useful electrical conductivity, particularly upon doping, created substantial interest in other types of electrically conducting polymers.

Conjugated poly(thiophenes) and substituted thiophene derivatives are also known to exhibit electrical conductivity. Such polymers can be cast into films and doped with conventional p- and n-type dopants or the doped polymers can be cast into films and their electrical properties modified accordingly. The resulting cast films are suitable for use in a variety of optoelectronic applications.

US2004/0010115A1, a patent application from which the present continuation-in-part application claims priority, discloses homopolymers and copolymers comprising repeating units of thieno[3,4-b]thiophene for use in electroactive applications. Water-borne dispersions of such polymers and copolymers can be cast by conventional methods to provide uniform, thin films which possess utility in numerous electroactive applications including electrochromic displays, optically transparent electrodes and antistatic coatings.

U.S. Pat. No. 6,645,401 B2 discloses conjugated polymers of dithienothiophene (DTT) with vinylene or acetylene connecting groups for use in semiconductors and charge transport materials for incorporation into electrooptical and electronic devices including field effect transistors, photovoltaic, and sensor devices. Polymers containing DTT formed by electrochemical polymerization are known but demonstrate limited solubility in solvents suitable for use in preparing electrooptical and electronic devices and generally inadequate photovoltaic properties.

U.S. Pat. No. 6,585,914 B2 discloses fluorocarbon-functionalized and/or heterocyclic modified poly(thiophenes), in particular, α, ω-diperfluorohexylsexithiophene for use in forming films which behave as n-type semiconductors. These poly(thiophenes) also can be used to form thin film transistors with FET mobility.

U.S. Pat. No. 6,676,857 B2 discloses mono-, oligo- and polymers having polymerized units of 3-substituted-4-fluorothiophene as liquid crystal materials for use in semiconductors, charge transport materials, electrooptical field effect transistors, photovoltaic and sensor devices.

U.S. Pat. No. 6,695,978 B2 discloses mono-, oligo- and polymers of benzo[b]thiophene and bisbenzo[b]-thiophene and their use as semiconductors and as charge transport materials in electrooptical devices.

U.S. Pat. No. 6,709,808 B2 discloses image forming materials incorporating electrically conductive polymers based upon pyrrole-containing thiophene polymers and aniline containing polymers.

J. P. Ferraris and coworkers in *Synthesis and Electronic Properties of Poly(2-phenyl-thieno[3,4-b]thiophene)*, Chem. Mater. 1999 11, 1957-1958, report a synthetic preparation of the referenced composition of matter and its electronic properties.

M. Pomerantz and coworker in *Poly(2-decyl-thieno[3,4-b]thiophene): a New Soluble Low-Band Gap Conducting Polymer*, Synthetic Materials 84 (1997) 243-244 disclose a soluble low-bandgap conducting polymer, poly(2-decyl-thieno[3,4-b]thiophene), and a process for preparing the polymer.

The disclosure of the previously identified patents, patent applications and publications is hereby incorporated by reference.

BRIEF SUMMARY OF THE INVENTION

This invention presents monomeric compositions of matter embodying thienothiophene having a partially or fully fluorinated alkyl group in the 2-position and to oligomers and polymers formed by polymerizing such thienothiophene monomers. Such polymers demonstrate improved processability and electrical properties for application as hole injection materials, charge transport materials and as semiconductors for use in optical, electrooptical or electronic devices, polymeric light emitting diodes (PLED), electroluminescent devices, organic field effect transistors (FET or OFET), flat panel display applications (i.e. LCD's), radio frequency identification (RFID) tags, ultracapacitors, organic photovoltaics (OPV's), sensors, in small molecule or polymer based memory devices, and in electrolytic capacitors and as hydrogen storage material.

The partially or fully fluorinated alkyl monomeric compositions of matter of the present invention are represented by the formula

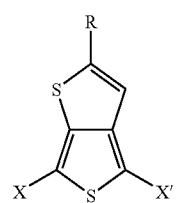

Formula 1 wherein

R is a partially or fully fluorinated primary, secondary or tertiary alkyl having from 1 to 8 carbon atoms; and X and X' are independently selected from the group consisting of H, F, Cl, Br, I, MgCl,

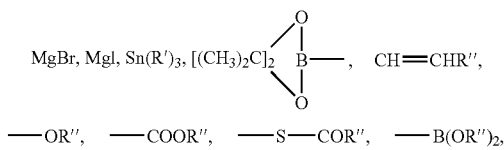

—COR″, —C≡CH, and a polymerizable cyclic pi-conjugated carbon-ring structure optionally comprising S, N or O heteroatoms;

wherein

R′ is a primary, secondary or tertiary alkyl having from 1 to 6 carbon atoms, and R″ is H or a primary, secondary or tertiary alkyl having from 1 to 6 carbon atoms.

The fully fluorinated alkyl monomeric compositions of matter of the present invention, commonly referred to as perfluorinated compositions, are represented by the formula

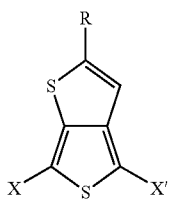

Formula 2 wherein

R is a fully fluorinated primary, secondary or tertiary alkyl having from 1 to 8 carbon atoms; and X and X′ are independently selected from the group consisting of H, F, Cl, Br, I, MgCl,

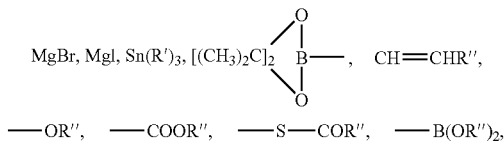

—COR″, —C≡CH, and a polymerizable cyclic pi-conjugated carbon-ring structure optionally comprising S, N or O heteroatoms;

wherein

R′ is a primary, secondary or tertiary alkyl having from 1 to 6 carbon atoms, and R″ is H or a primary, secondary or tertiary alkyl having from 1 to 6 carbon atoms.

In another embodiment, the compositions of Formula 2 are disclosed wherein X is H, X′ is H and R is a fully fluorinated primary, secondary or tertiary alkyl having 4 carbon atoms. In another embodiment, the composition of matter of Formula 2 are presented wherein at least one of X and X′ is represented by the formulae

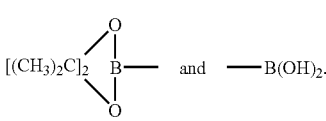

Formula 3

In another alternate embodiment, the compositions of matter of Formula 2 are presented wherein at least one of X and X′ is selected form the group consisting of F, Cl, Br and I. Preferably, at least one of X and X′ is Br.

In another alternate embodiment, the compositions of Formula 2 are presented wherein at least one of X and X′ is —CH═CH2.

In another alternate embodiment, the compositions of Formula 2 are presented wherein at least one of X and X′ is —C≡CH.

In another alternate embodiment, the compositions of Formula 2 are presented wherein at least one of X and X′ is Sn(R′)3.

In another alternate embodiment, the compositions of Formula 2 are presented wherein at least one of X and X′ is a polymerizable cyclic pi-conjugated carbon-ring structure optionally comprising S, N or O heteroatoms. Preferably, the polymerizable cyclic pi-conjugated carbon-ring structure consists of a pi-conjugated single carbon-ring structure optionally comprising S, N, or O heteroatoms. More preferably, the polymerizable cyclic pi-conjugated carbon-ring structure consists of a pi-conjugated two or three fused carbon-ring structure optionally comprising S, N or O heteroatoms. More preferably, at least one of X and X′ is selected from the group consisting of phenyl, naphthyl, pyrryl, dithienyl, thienyl and their substituted derivatives. Most preferably, at least one of X and X′ is thieno[3,4-b]thiophene or at least one of X and X′ is thieno[2,3-b]thiophene.

The partially or fully fluorinated alkyl polymeric compositions of matter (defined to include dimers and oligomers) of the present invention are represented by the formula Formula 4 wherein

R is a fully fluorinated primary, secondary or tertiary alkyl having from 1 to 8 carbon atoms, n is an integer, Y is —CZ$^1$=CZ$^2$—, —C≡C— phenyl, naphthyl, pyrryl, thienyl, thieno[3,4,b]thiophene, thieno[2,3-b]thiophene and their respective substituted derivatives, and Z$^1$ and Z$^2$ are independently selected from H, F, Cl or CN.

The polymeric compositions of Formula 4 include dimers and oligomers wherein n is an integer from 2 to 10, inclusive, and polymers wherein n is an integer from 11 to 50,000, inclusive.

An alternate embodiment of Formula 4 presents compositions wherein Y is —CH═CH—. Another alternate embodiment of Formula 4 presents compositions wherein Y is —C≡C—.

An alternate embodiment of Formula 4 presents compositions wherein Y is selected from the group consisting of phenyl, naphthyl, pyrryl, thienyl, thieno[3,4,b]thiophene, thieno[2,3-b]thiophene and their respective substituted derivatives.

The compositions of Formula 4 can be treated with conventional dopants such as p-type and n-type dopants.

The compositions of Formula 4 can be prepared as dispersions by combining one or more compositions with a fluid in which such compositions are partially or fully soluble in a given amount of such fluid. Suitable fluids include water, polyacrylic acid, polymethacrylic acid, polymaleic acid, polystyrene sulfonic acid, a perfluorosulfonic acid polymer and polyvinyl sulfonic acid, poly(styrene-co-acrylonitrile) sulfonic acid and mixtures thereof.

Preferred polymeric compositions of the presented invention (defined as including dimers and oligomers) are represented by the formula:

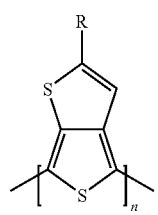

Formula 5 where R is a fully fluorinated primary, secondary or tertiary alkyl having from 1 to 8 carbon atoms and n is an integer from 2 to 50,000, inclusive.

An alternate embodiment of Formula 5 presents compositions wherein R is trifluoromethyl, perfluoroethyl, perfluoropropyl, perfluorobutyl, 2,2,2-trifluoromethyl-ethyl and 2,2,2-trifluoro-1,1-bis-trifluoromethyl-ethyl. Preferably, R is perfluorobutyl.

The compositions of Formula 5 can be treated with conventional dopants such as p-type and n-type dopants.

The compositions of Formula 5 can be prepared as dispersions by combining one or more compositions with a fluid in which such compositions are partially or fully soluble in a given amount of such fluid as set forth in the Detailed Description of the Invention.

DETAILED DESCRIPTION OF THE INVENTION

I. Definitions

For purposes of interpreting the Specification and appended claims, the following terms shall be given the meaning set forth below:

The term, alkyl, shall mean a paraffinic hydrocarbon group which may be derived from an alkane by dropping one hydrogen from the formula. Non-inclusive examples are methyl ($CH_3$—), ethyl ($C_2H_5$—), propyl ($CH_3CH_2CH_2$—), isopropyl (($CH_3)_2CH$—).

The term, partially fluorinated alkyl, shall mean a paraffinic hydrocarbon group wherein at least one, but not all hydrogen atoms of the alkyl have been replaced with a fluorine atom.

The term, fully fluorinated alkyl, shall mean a paraffinic hydrocarbon group wherein at each hydrogen atom of the alkyl has been replaced with a fluorine atom. A synonym is a perfluorinated alkyl.

The term, halogen, shall mean one of the electronegative elements of group VIIA of the periodic table (fluorine, chlorine, bromine and iodine).

The term, sulfoxyl, shall mean a group of composition RS(O)— where R is an alkyl, aryl, cycloalkyl, perfluoroalkyl or perfluoroaryl group. Examples include, but are not limited to methylsulfoxyl, phenylsulfoxyl, and the like.

The term, sulfonyl, shall mean a group of composition $RSO_2$— where R is an alkyl, aryl, cycloalkyl, perfluoroalkyl, or perfluoroaryl group. Examples include, but are not limited to methylsulfonyl, phenylsulfonyl, p-toluenesulfonyl, and the like.

The term, acyl, shall mean an organic acid group in which the —OH of the carboxyl group is replaced by another substituent (RCO—). Examples include, but are not limited to acetyl, benzoyl, and the like.

The term, polymerizable cyclic pi-conjugated carbon-ring structure, shall mean a single ring structure formed of carbon atoms, and optionally heteroatoms as set forth in this Specification, or fused ring structures consisting of two or three rings, and optionally heteroatoms as set forth in this Specification wherein the atoms of such ring structures are pi-conjugated resulting in electronic delocalization within the ring structures. An example of a single ring structure is benzene, an example of a fused two-ring structure is naphthalene and an example of a fused three-ring structure is anthracene.

The term, fluid, shall mean a form of matter that cannot permanently resist any shearing force, which causes flow.

The term, polymer, shall mean a composition of matter having from 2 to 50,000 repeating units, n, of a partially or fully fluorinated alkyl-thieno[3,4-b]thiophene set forth in Formulae 4 and 5 of the Specification. The term, polymer, includes homopolymers, copolymers, oligomers and dimers.

The term, substrate, shall mean a solid material (which may be flexible or rigid) suitable for deposition of the compositions of matter according to this invention. Substrates can be formed of materials including, but not limited to glass, organic polymers, plastic, silicon, minerals, semiconducting materials, ceramics, metals and the like. The substrate may be inherently conductive.

The term, electroactive monomer, shall mean a monomer which is capable of polymerization or copolymerization resulting in a polymer having electrical/electronic properties such as electrical conductivity, semiconductivity, electroluminescence, electrochromicity or photovoltaic properties.

The term, non-electroactive monomer, shall mean a monomer which is capable of polymerization or copolymerization which does not exhibit the properties set forth under the definition of electroactive monomer.

The term, band gap, shall mean the energy difference between electronic energy levels called the conduction band and the valence band.

The term, substituted, as used with respect to a composition of matter, shall mean an electron-rich or electron deficient group appended to such composition of matter. A substituted composition of matter shall be referred to as a substituted derivative thereof.

II. Description

The monomers of the present invention can be propagated to form polymerized units by effecting reaction at positions X and X' to provide a polymer which demonstrates a variety of uses as described in this Specification. The monomers of Formula 1 as set forth in the Brief Summary of the Invention can be conveniently prepared by following the general procedure set forth in the Examples of this Specification without undue experimentation by substituting the appropriate starting materials for those used in the Examples to provide the desired compositions of matter.

For example, when positions X and X' of the monomers set forth in Formula 1 are hydrogen atom, such monomers can react with additional monomers of the same composition according to Formula 1 to form a homopolymer of polymerized units. Alternately, such compositions wherein X and X' are hydrogen atoms can react with one or more additional electroactive monomers or non-electroactive monomers to form copolymers, including random copolymers, graft copolymers, block copolymers, and dendritic structures.

Electroactive monomers suitable for incorporation into the polymers of this invention to form copolymers include those monomers known in the art which exhibit electroactivity, including but not limited to thiophene, substituted thiophenes, substituted thieno[3,4-b]thiophenes, dithieno[3,4-b,3',4'-d]thiophene, pyrrole, bithiophene, substituted pyrroles, phenylene, substituted phenylenes, naphthalene, substituted naphthalenes, biphenyl and terphenyl and their substituted versions, phenylene vinylene and substituted phenylene vinylene.

Suitable substituted thieno[3,4-b]thiophenes for incorporation into the polymers of the present invention to form copolymers are represented by the formula:

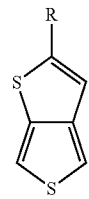

wherein R=C1 to C12 primary, secondary or tertiary alkyl groups, phenyl and substituted phenyl groups, cyclohexyl, naphthalenic, hydroxyl, alkyl ether, carboxylic acids, esters and sulfonic acid groups.

Suitable substituted thiophenes for incorporation into the polymers of the present invention to form copolymers include the following substituted thiophenes described in U.S. Pat. No. 4,959,430 (hereby incorporated by reference):

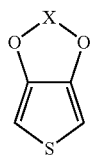

where x denotes a substituted C1-C4 alkyl group, a C1-C12 alkyl or phenyl substituted 1,2 ethylene radical or a 1,2 cyclohexylene radical. Optionally, the alkyl or phenyl groups can be further substituted with functional groups such as hydroxyls, ethers and the like.

Additional substituted thiophenes for incorporation into the polymers of the present invention to form copolymers include the following substituted thiophenes presented in U.S. Pat. No. 4,910,645:

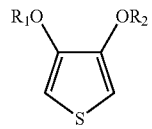

wherein R1 and R2 are independently selected from the group consisting of H, C1-C4 alkyl groups, 1,2 cyclohexylene radical and phenyl substituted phenyl.

The compositions of matter of the present invention may also include repeating units of non-electroactive monomers which are capable of being polymerized with thieno[3,4-b]thiophene provided that the presence of such non-electroactive monomers does not adversely affect the electroactive properties of the resulting composition of matter.

The compositions of matter of this invention can be utilized as dispersions by combining a desired polymer (including copolymers and oligomers) with a fluid as set forth in the Brief Summary of the Invention.

Dispersions containing the polymeric compositions of matter according to Formulae 4 and 5 of this invention can be applied via conventional processes including ink jet printing, screen printing, roll to roll printing processes, spin coating, meniscus and dip coating, spray coating, brush coating, doctor blade application, curtain casting and the like.

The amount of polymer (including copolymers and oligomers) to be incorporated into the solution or dispersion shall vary depending upon a variety of factors including the molecular weight of the composition of matter and the end-use application. The actual amount of composition of matter to be introduced into the dispersion is readily determined without undue experimentation.

The dispersed films may be dried by conventional techniques including evaporation to remove the solvent to provide the desired film. Drying may be effected at room temperature or any temperature which does not adversely affect the properties of the resulting film. However, to obtain higher processing speeds, the film can be dried at elevated temperatures provided that such temperatures do not adversely affect the properties of the resulting film.

The compositions of matter of this invention can be utilized in a variety of conventional applications including antistatic coatings, electrically conductive coatings, electrochromic devices, photovoltaic devices, light emitting diodes, flat panel displays, photoimageable circuits, printable circuits, thin film transistor devices, batteries, electrical switches, capacitor coatings, corrosion resistant coatings, electromagnetic shielding, sensors, LED lighting and the like. The electrical conductivity of the compositions of matter according to the present invention can be readily modified, if necessary, to meet the requirements of any of the previously mentioned application by doping these compositions of matter with conventional acidic dopants (p-dopants) and basic dopants (n-dopants) known in the art.

Suitable p-dopants include mineral acids such as HCl, $HNO_3$, $H_2SO_4$, $H_3PO_4$, HBr, HI; organic sulfonic acids such as dodecyl benzene sulfonic acid, lauryl sulfonic acid, camphor sulfonic acid, organic acid dyes, methane sulfonic acid, toluene sulfonic acid, polymeric sulfonic acids such as poly(styrene sulfonic acid) and copolymers; carboxylic acids such as adipic acid, azelaic acid, oxalic acid, and polymeric polycarboxylic acids such as poly(acrylic acid) poly(maleic acid), poly(methacrylic acid) and copolymers containing these acids. Conventional mixed dopants such as mineral acids/ organic acids can also be utilized to impart desired electroactive character to the compositions of matter of this invention.

While p-doping is generally preferred, the compositions of matter according to this invention can be n-doped with conventional basic dopants including but not limited to Na, K, Li and Ca.

The compositions of matter of Formulae 4 and 5 of this invention are well suited for use in fabricating certain components of light emitting diodes (LEDs). LEDs typically possess numerous layers including a substrate, and indium tin oxide (ITO) anode, a hole injection layer, a hole transport layer, a light emitting layer, an electron transport layer, an electron injection layer and a cathode. The p-doped compositions of matter of this invention are particularly suited toward replacing the indium tin oxide anode of the LED. The p-doped compositions of matter of this invention are also particularly suited toward use as the hole injection layer of the LED. Undoped compositions of matter of this invention can be utilized in the hole transport layer, the light emitting layer and/or the electron transport layer of the LED.

Admixtures of the compositions of matter of this invention with other electroactive materials such as laser dyes, other electroactive polymers, hole transport or electron transport materials including electroactive organometallic compounds are also embodied in this invention.

Photovoltaic devices have specific similarities to LEDs. Instead of electrical voltage placed across the device to produce light for the LED device, the input of light (e.g. sunlight) produces a voltage difference across the device to produce an electric current. The layers of the LED and photovoltaic devices are similar but not equivalent. Light harvesting organics or polymers comprise an intermediate layer with hole transport/electron transport layers optionally placed between the anode and cathode. The compositions of matter of this invention can be utilized as the anode and hole injection layers (doped) or in the light harvesting layers (undoped).

The compositions of matter according to this invention can be utilized in fabricating electrochromic devices which permit or prevent the transmission of light through transparent substrates by application of a voltage across conventional substrates known in the art. Other uses for the compositions of matter according to the present invention include electromagnetic shielding and dimmable mirrors.

The doped compositions of matter according to this invention can be utilized as antistatic coatings applied from waterborne or organic solvent-borne solutions or dispersions to substrates enumerated under the definition section. Such antistatic coatings can include admixtures with other polymers including emulsions to achieve a balance of conductivity and film properties such as adhesion to the appropriate substrate. The compositions of matter of this invention can also be utilized as coatings or additives to various articles of commerce to render the article conductive including the various substrates noted above for antistatic coatings and electroplating processes, printable circuits, photoimageable circuits, semiconductor devices and the like.

While the preferred embodiment of this invention involves use of the compositions of matters as transparent/conductive materials, conductive nontransparent coatings based on the compositions of matter of this invention are also believed to have utility in specific applications where transparency is not important but electrical conductivity is important. Certain applications such as antistatic coatings may require pigmentation which will result in loss of transparency as well as various conductive paint applications. Printed circuits employing these materials will also generally not require transparency.

The compositions of matter of this invention can also be utilized to prepare optically transparent conductive coatings for use in optically transparent electrodes, transparent conductive adhesives, stealth coatings, transparent EMF shielding, touch screens, flat screen displays, flat antennas for mobile applications, transparent capacitor plates, and the like.

Additives such as ethylene glycol, diethylene glycol, mannitol, propylene 1,3-glycol, butane 1,4-glycol, N-methyl pyrrolidone, sorbitol, glycerol, propylene carbonate and other appropriate high boiling organics may be added to dispersions of the compositions of matter of this invention to improve conductivity.

Additional additives include conductive fillers such as particulate copper, silver, nickel, aluminum, carbon black and the like. Non-conductive fillers such as talc, mica, wollastonite, silica, clay, $TiO_2$, dyes, pigments and the like can also be added to the dispersions to promote specific properties such as increased modulus, surface hardness, surface color and the like.

The dispersions of the compositions of matter of this invention may also comprise antioxidants, UV stabilizers and surfactants when required for specific applications. Surfactants are typically added to the dispersions to control stability, surface tension, and surface wettability. Preferred surfactants include acetylenic diols. Viscosity modifiers (such as associative thickeners) can also be added to such dispersions to adjust viscosity for specific end uses.

The compositions of matter according to the present invention can be conveniently prepared by a variety of methods. The compositions of matter according to the present invention are preferably prepared utilizing an aqueous phase polymerization method wherein the desired thieno[3,4-b] thiophene, a polyanion and an oxidant are reacted in the presence of water under reaction conditions sufficient to form the corresponding polymer. The temperature for conducting the polymerization is not critical but affects the rate of polymerization.

Typical reaction conditions include temperatures ranging from 0° to about 50° C. The polymerization is continued for a period of time until the reaction in completed to effect the desired degree of polymerization. The degree of polymerization is not a critical element of this invention, but shall vary depending upon the end use application. The desired degree of polymerization shall depend upon the end use as is readily determined by one of ordinary skill in the art without undue experimentation. The polymerization time may range between a few minutes up to about 48 hours and depends on a number of factors including the size of the reactor utilized in the polymerization, the polymerization temperature and the oxidant utilized in the polymerization process.

The amount of polyanion and oxidant to be employed in the aqueous polymerization method may broadly vary and can be determined for any given polymerization without undue experimentation. For example, the weight ratio of monomers according to this invention to a desired polyanion typically ranges from 0.001 to 50, preferably 0.05 to 2.0. The weight ratio of monomers of this invention to a desired oxidant typically ranges from 0.01 to 10 preferably 0.1 to 2.0. In the case of ferric sulfate, the amount used ranges from 0.1 to 5 of monomers of this invention.

Suitable polyanions include an anion of a polycarboxylic acid, such as polyacrylic acid, polymethacrylic acid, NAFION, a perfluorosulfonic acid polymer (NAFION is a registered trademark of E.I. DuPont de Nemours & Co., Wilmington, Del.), polymaleic acid, and polymeric sulfonic acids, such as polystyrene sulfonic acid and polyvinyl sulfonic acid. The polycarboxylic and polysulfonic acids may also be copolymers of vinyl carboxylic and vinyl sulfonic acids with other monomers, such as acrylates and styrene. The molecular weight of the acids supplying the polyanions is preferably in the range from 1,000 to 500,000, preferably from 2000 to 500,000. The acids from which the polyanions are derived are commercially available or may be produced by known methods.

Suitable oxidants include iron (III) salts, such as FeCl3, Fe(ClO4)3 and the iron (III) salts of organic acids and inorganic acids containing organic residues, H2O2, K2Cr2O7, alkali or ammonium persulfates, alkali perborates, potassium permanganate and copper salts such as copper tetrafluoroborate. In addition iodine, air and oxygen may advantageously be used as oxidants. Persulfates and the iron (III) salts of organic acids and inorganic acids containing organic residues are preferred because they are not corrosive.

Examples of iron (III) salts of organic acids are the Fe(III) salts of C1-30 alkyl sulfonic acids, such as methane or dodecane sulfonic acid; aliphatic C1-20 carboxylic acids, such as 2-ethylhexylcarboxylic acid, aliphatic perfluorocarboxylic acids, such as trifluoroacetic acid and perfluorooctanoic acid; aliphatic dicarboxylic acids, such as oxalic acid and, aromatic, optionally C1-20-alkyl-substituted sulfonic acids, such as benzenesulfonic acid, p-toluene-sulfonic acid and dodecyl benzenesulfonic acid and mixtures of the aforementioned Fe(III) salts of organic acids. Examples of iron (III) salts of inorganic acids containing organic residues are the iron (III) salts of sulfuric acid semiesters of C1-20 alkanols, for example the Fe(III) salt of lauryl sulfate.

An alternate method according to this invention for preparing the polymers of this invention involves an electrochemical process wherein the desired monomer is polymerized in an electrochemical cell using a three electrode configuration. A suitable three electrode configuration comprises a button working electrode selected from the group consisting of platinum, gold and vitreous carbon button working electrodes, a platinum flag counter electrode and an Ag/Ag+ non-aqueous reference electrode. Suitable electrolytes are selected from the group consisting of tetrabutylammonium perchlorate/acetonitrile, lithium triflate/acetonitrile and tetrabutylammonium hexafluorophosphate/acetonitrile.

Conventional electrolytic cells can be utilized to practice the electrochemical process for making the compositions of matter of the present invention. The preferred working electrode for making the compositions of matter of this invention is a vitreous carbon electrode and the preferred electrolyte is tetrabutylammonium perchlorate/acetonitrile.

The monomers of this invention can also be electrochemically polymerized in the presence of sodium poly(styrene sulfonate) using cyclovoltammetric polymerization. Polymerization was evident as indicated by the increase in current response for the lower redox process which corresponds to the reduction and oxidation of the conducting polymer that had been electroprecipitated onto the electrode surface. After electrochemical polymerization, the electrode was removed from the electrolyte, washed with brine and then placed into a 0.5M NaCl/H$_2$O solution.

The preferred oxidative polymerization method is carried out in aqueous solution utilizing poly(styrene sulfonic acid) or a perflurorsulfonic acid polymer as the polyanion and ammonium/persulfate and/or iron (III) sulfate as the chemical oxidant.

The polymerization has been described as a homopolymerization but it is also possible to conduct a copolymerization of a desired monomer of this invention with another monomer such as 3,4ethylenedioxythiophene or pyrrole.

Synthesis of 2-(perfluorobutyl)-thieno[3,4-b]thiophene, for example, can be effected by the 5 step process.

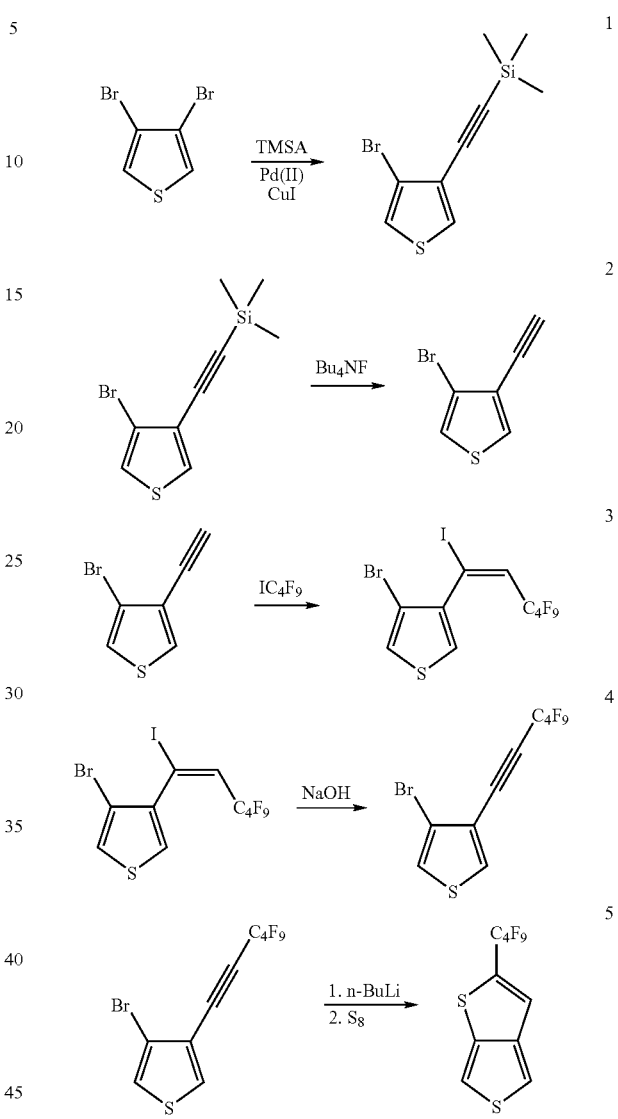

Many of the derivatives of the respective monomers where X and X' are other than H are formed post formation of the monomers. In post reaction one or both hydrogen atoms may be replaced with other functional groups. Alternatively, some of the derivatives may be formed, ab initio, by converting thiophene to the derivative and then undergoing the 5 step reaction procedure where the X and X' are compatible with the chemistries outlined in steps 1-5 above.

The polymers of this invention include irregular polymers and regioregular polymers. Regioregular means that the polymerization units are bonded in a head to tail, that is, the 6-position of a first polymerizable unit is bonded to the 4-position of a second polymerizable unit and the 6-position of the second polymerizable unit is bonded to the 4-position of the third polymerizable unit and so on.

Polymerization of 2-(perfluorobutyl)-thieno[3,4-b] thiophene monomer can be effected utilizing an aqueous phase polymerization method wherein the monomer 2-(perfluorobutyl)-thieno[3,4-b]thiophene, a polyanion and an oxidant are reacted in the presence of water under reaction conditions sufficient to form the homopolymer, e.g., poly(2-(perfluorobutyl)-thieno[3,4-b]thiophene). By this polymerization process, the resulting polymer may be polymerized and doped in a single step.

The amount of polyanion and oxidant to be employed in the aqueous polymerization method may broadly vary and can be determined for any given polymerization without undue experimentation. For example the weight ratio of 2-(perfluorobutyl)-thieno[3,4-b]thiophene monomer to a desired polyanion typically ranges from 0.001 to 50, preferably 0.05 to 2.0. The weight ratio of 2-(perfluorobutyl)-thieno[3,4-b]thiophene monomer to a desired oxidant typically ranges from 0.01 to 10 preferably 0.1 to 2.0. For example, when ferric sulfate is used as the oxidant the amount used ranges from 0.1 to 5 of 2-(perfluorobutyl)-thieno[3,4-b]thiophene. The nature of the oxidant may be varied in order to address variants in the ionization potential of the utilized monomers. Various Fe(II)/Fe(II) couplets are known that display different potential depending on their respective ligands, e.g., $FeCl_3$; $Fe_2(S_2O_8)_3$; $Fe(phen)_3$. If weaker oxidants are required Cu based couplets may be considered. If stronger oxidants are needed Co based couplets should be considered.

The monomers set forth in Formula 1 of this Specification can be polymerized utilizing conventional metal-catalyzed polymerization methods described in the open literature. One of ordinary skill shall vary the conditions depending on the nature of the X and X' substituents to yield the desired polymer without undue experimentation.

Films of the polymers of this invention may be doped with conventional p- and n-type dopants post polymerization of the respective monomers. The doping process typically involves treatment of the film semiconductor material with an oxidizing or reducing agent in a redox reaction to form delocalized ionic centers in the material, with the corresponding counterions derived from the applied dopants. Doping methods comprise for example exposure to a doping vapor in the atmospheric or at a reduced pressure, electrochemical doping in a solution containing a dopant, bringing the dopant in contact with the semiconductor material to be thermally diffused, and ion-implantation of the dopant into the semiconductor material.

III. EXAMPLES

The following examples are provided to illustrate various embodiments and comparisons and are not intended to restrict the scope of the invention.

Example 1

Preparation of 2-(perfluorobutyl)-thieno[3,4-b]thiophene 2-(perfluorobutyl)-thieno[3,4-b]thiophene is prepared by a 5 step procedure in the manner described.

Step 1
Preparation of 3-bromo-4-(trimethylsilylethynyl)thiophene

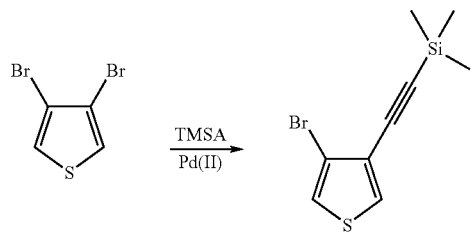

A 2-liter round-bottomed, three-necked flask was equipped with a reflux condenser, a mechanical stirrer, and a thermocouple, then purged with dry nitrogen gas. The flask was then charged with 240 g of diethylamine (previously dried over KOH pellets and filtered), 387.04 g (1.60 mol.) of 3,4-dibromothiophene, 800 mg (3.04 mmol) triphenylphosphine, 600 mg (5.48 mmol) of copper(I)iodide, and a 78.56 g (0.80 mol.) portion of trimethylsilylacetylene. The stirred mixture was warmed to 40° C. A 2.00 g (2.8 mmol.) portion of dichlorobis(triphenylphosphine)palladium(II) was then added. The reaction was maintained at 40° C. for 4 hrs with mechanical stirring and a static nitrogen blanket. At that point the reaction mixture was deemed complete and the reaction mixture cooled to room temperature.

Recovery of the product, 3-bromo-4-(trimethylsilylethynyl)thiophene, was effected by placing the reaction mixture on a roto-evaporator and the diethylamine was removed by evaporation. A 600 ml portion of pentane was added to the residual from evaporation along with 40 g of activated carbon (Darco, 12-20 mesh). The pentane solution was then filtered through a silica gel column (100 g) to remove palladium, followed by 600 ml or more of pentane. The pentane solvent from the collected solution was removed via evaporation on a roto-evaporator. Mass of isolated crude product is approximately 316 g containing 142 g of 3-bromo-4-(trimethylsilylethynyl)thiophene. The residual material was vacuum distilled producing 129 g of 97.2% 3-bromo-4-(trimethylsilylethynyl)-thiophene (60.3% yield based on trimethylsilylacetylene). BP 37° C. at 740 mtorr. $^1$H-NMR: δ (ppm) 0.3 (s), 7.19, 7.45; $^{13}$C-NMR: δ (ppm) −0.1, 97, 113, 122, 123, 129.

Step 2

Preparation of 3-bromo-4-ethynylthiophene

The product of step one is converted to 3-bromo-4-ethynylthiophene according to the equation as follows:

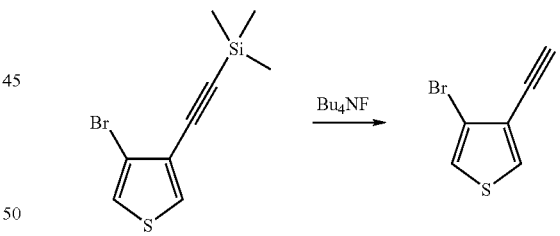

3-Bromo-4-(trimethylsilylethynyl)thiophene (10 g, 38 mmol) and THF (45 ml) was stirred and cooled to 2° C. Tetrabutylammonium fluoride (75 ml 1M in THF) was added slowly maintaining the temperature 0° to 5° C. After the addition was complete, the reaction is stirred for 30 minutes while allowing to warm to 20° C. Water (140 ml) was added to the flask and the product was stirred at 20° C. for 2 hours. The product was then extracted with 3×50 ml hexane. The combined hexane extract was washed with 40 ml of 10% HCl then water and dried over magnesium sulfate. The product was recovered as an orange liquid after the solvent was removed by rotary evaporation. After distillation, 6.5 g of 3-bromo-4-ethynylthiophene is recovered, (92% yield). Bp 58° C. at 1.5 mm Hg. $^1$H-NMR: δ (ppm) 7.4, 7.5, 7.7; $^{13}$C-NMR: δ (ppm) 77, 82, 114, 124, 125, 134.

Step 3

Preparation of 3-bromo-4-(1-iodo-2-perfluorobutyl-vinyl)thiophene)

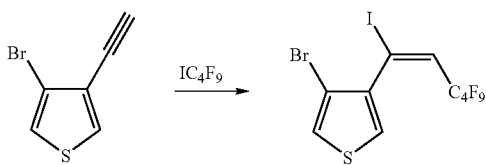

3-Bromo-4-ethynylthiophene (4.1 g, 22 mmol) and perfluorobutyliodide (15.16 g, 44 mmol) were stirred in a mixture of acetonitrile (80 ml) and water (50 ml) and cooled to 15° C. Sodium bicarbonate (2.4 g, 29 mmol) and sodium hydrosulfite (4.5 g, 26 mmol) were then added to the solution. After stirring 20 minutes the reaction was diluted with water (75 ml) and extracted with pentane. Pentane was removed from the product by rotary evaporation isolating about 10 g of a crude mixture. MS: m/z 407, 405, 207, 188, 157, 127, 69; $^1$H-NMR: δ (ppm) 6.7 (t, 1), 7.22 (d, 1), 7.27 (d, 1), $^{19}$F-NMR: δ (ppm) −80(s, 3), −107 (s, 2), −124 (s, 2), −126 (s, 2).

Step 4

Preparation of 3-bromo-4-(perfluorobutylethynyl)-thiophene

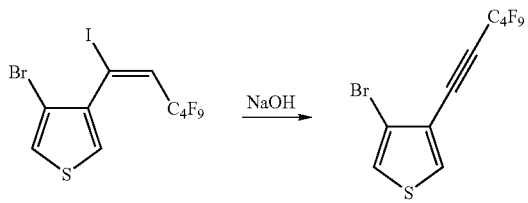

Sodium hydroxide (7 g, 175 mmol) dissolved in a 50/50 mixture of ethanol and water was added to the isolated product of Step 3. The reaction was stirred overnight at room temperature. The product was extracted with pentane and purified by distillation at 41° C., 300 mTorr. MS m/z 406, 404, 386, 384, 237, 235, 169, 156, 119, 111, 69; $^1$H-NMR: δ (ppm) 7.3 (d, 1), 7.8 (d, 1), $^{19}$F-NMR: δ (ppm) −80 (s, 3), −97 (s, 2), −124 (s, 2), −126 (s, 2)

Step 5

Preparation of 2-(perfluorobutyl)-thieno[3,4-b]thiophene

The product of Step 4 was converted to 2-(perfluorobutyl)-thieno[3,4-b]thiophene according to the equation as follows

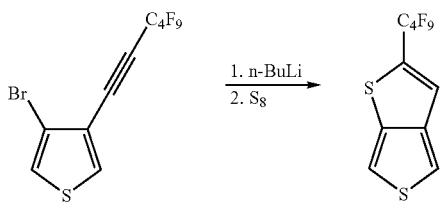

A mixture of 155 ml of diethyl ether and 9.45 g of 3-bromo-4-(perfluorobutylethynyl)-thiophene (0.0233 mol) was placed in a 500 ml round-bottomed, three-necked flask equipped with a thermometer, gas inlet, a magnetic stir bar, a gas outlet, and a septum sealed port. The air in the flask was completely replaced by nitrogen, after which the solution was cooled to −73° C.

A solution of a 9.5 ml of 2.5 Molar n-butyl lithium (0.0238 mol) in hexane was added over 5 minutes by syringe through the septum, white keeping the reaction temperature below −70° C. Twenty five minutes after completion of n-butyl lithium addition, and with reaction temperature maintained at −72 to −75° C., 0.761 g of dry, powdered sulfur (0.0238 mol) was added over a few seconds. After one hour at less than −72° C., 155 ml of methanol, at approx −50° C. was added to the reaction mix and the reaction allowed to warm to room temperature over about one hr. Solvent was stripped from the reaction mixture at 35° C.

The residue was suspended/dissolved in 155 ml of hexane, cooled to −78° C. under nitrogen, and 10 ml of 2.5M n-butyl lithium added over one minute. Over the next 30 minutes to mix was allowed to warm to −50° C., and held at −50° C. for another 30 minutes. The lithiation is quenched by addition of 155 ml of methanol. Solvent was stripped at 35° C. and the residue suspended/dissolved in 50 ml of diethyl ether. Solids were removed by centrifugation, and washed twice with ether. Ether extracts were combined, producing a solution containing 5.7 g of 2-(perfluorobutyl)-thieno[3,4-b]thiophene, and the ether was stripped at 35° C.

The product was Kugelrohr distilled (55° C. pot temperature), using a room temperature receiver. The distillate was re-distilled on a short path still in a 50-56° C. oil bath. The 3.0 g heart cut, contained 97.2% 2-(perfluorobutyl)-thieno[3,4-b]thiophene (35.4% isolated yield). BP 36° C. at 160 mtorr; MS m/z 358, 189, 359, 339, 191, 360, 220; $^1$H-NMR (CDCl$_3$): δ (ppm); 7.3 (s, 2), 7.6 (s, 1); $^{13}$C-NMR: δ (ppm) 111 (s, 1), 116 (s, 1), 120 (s, 1), 135 (t, 1), 138 (s, 1), 145 (s, 1); multiplets at 106, 108, 110, 112, 114, 116, 118 (4); $^{19}$F-NMR: δ (ppm) −82 (s, 3), −105 (s, 2), −123 (s, 2), −127 (s, 2).

Example 2

Preparation of 3-bromo-4-(1-iodo-2-trifluoromethyl-vinyl)thiophene

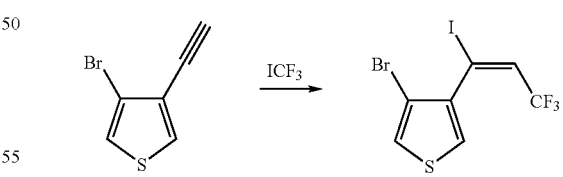

3-Bromo-4-ethynylthiophene (4.0 g, 22 mmol), acetonitrile (60 ml), water (20 ml) and sodium bicarbonate (2.5 g, 29 mmol) were charged to a 300 cc stainless steel Parr reactor. The solution was cooled to −35° C. and de-gassed. Trifluoromethyl iodide (26 mmol) was condensed into the reactor. Sodium hydrosulfite (4.6 g, 26 mmol) dissolved in water (20 ml) was then added to the reaction and stirred for two hours. Additional trifluoromethyl iodide (26 mmol) was condensed into the reactor and stirred for one hour. The reaction was diluted with water and extracted with pentane. Pentane was removed from the product by rotary evaporation. MS: m/z 384, 382, 284, 257, 255, 176, 157, 127, 107, 69.

Example 3

Preparation of 3-bromo-4-(trifluoromethylethynyl)thiophene

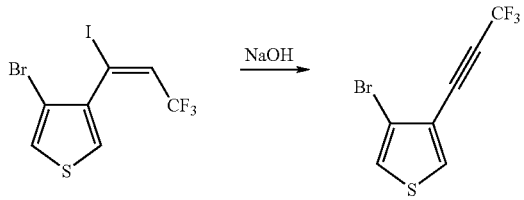

Sodium hydroxide (1.2 g, 30 mmol) dissolved in a 50/50 mixture of ethanol and water was added to the product of Example 2. The reaction was stirred overnight at room temperature. The product was extracted with pentane and purified by distillation at 25° C., 300 mTorr. MS: m/z 256, 254, 236, 234, 206, 204, 175, 131, 106, 99, 69 $^1$H-NMR: δ (ppm) 7.3 (d, 1), 7.7 (d, 1); $^{19}$F-NMR: δ (ppm) −50 (s, 3)

Example 4

Electrochemical Polymerization of 2-(perfluorobutyl)-thieno[3,4-b]thiophene 2-(perfluorobutyl)-thieno[3,4-b]thiophene was dissolved in 100 mM tetrabutylammonium hexafluorophosphate/anhydrous acetonitrile solution to a concentration of 10 mM monomer and was electrochemically polymerized employing a 3-electrode configuration, using an ITO working electrode (1 cm$^2$ Delta Technologies, Limited, $R_s$=5-15 Ohm, CG-50IN-CUV), platinum flag counter electrode (1 cm$^2$), and a Ag/Ag+ nonaqueous reference electrode. The reference electrode (Bioanalytical Systems, Inc.; MF-2062) consisted of a Ag wire in a 0.1 M AgNO$_3$ anhydrous acetonitrile solution. A CH Intruments Model 700B Series Electrochemical Analyzer/Workstation was utilized to drive the electrochemical polymerization at room temperature under a blanket of nitrogen. The applied potential was cycled between 1.6V and 0V at a rate of 100 mV/sec.

Polymerization was apparent from the development of a blue film on the surface of the transparent ITO electrode.

Example 5

Electrochemical Synthesis of Poly(2-perfluorobutyl)-thieno[3,4-b]thiophene)

2-perfluorobutyl)-thieno[3,4-b]thiophene was dissolved in 100 mM tetrabutylammonium hexafluorophosphate/anhydrous acetonitrile solution to a concentration of 10 mM monomer and was electrochemically polymerized employing a 3-electrode configuration, using an ITO working electrode (1 cm$^2$, Delta Technologies, Limited, $R_s$=5-15 Ohm; CG-50IN-CUV), platinum flag counter electrode (1 cm$^2$), and a Ag/Ag+ nonaqueous reference electrode. The reference electrode (Bioanalytical Systems, Inc.; MF-2062) consisted of a Ag wire in a 0.1 M AgNO$_3$ anhydrous acetonitrile solution. A CH Intruments Model 700B Series Electrochemical Analyzer/Workstation was utilized to drive the electrochemical polymerization at room temperature under a blanket of nitrogen. The applied potential was kept constant at 1.4V for 30 seconds.

Polymerization was apparent from the development of a blue film on the surface of the transparent ITO electrode

Example 6

Copolymerization of 2-(perfluorobutyl)-thieno[3,4-b]thiophene and 3,4-ethylenedioxythiophene A copolymer of 2-(perfluorobutyl)-thieno[3,4-b] thiophene and 3,4-ethylenedioxthiophene was prepared according to the procedure set forth in Example 4 except that a solution was prepared consisting of 5 mM 2-(perfluorobutyl)-thieno[3,4-b]thiophene and 5 mM ethylenedioxythiophene in 0.1 M tetrabutylammonium hexafluorophosphate (TBAPF6)/ACN. Polymerization was evidenced by the increase in current of the lower redox process upon sequential scanning and the onset of oxidation of the formed copolymer as measured by Cyclic Voltammetry. The copolymer displayed an onset of −0.5 V against Ag/AgNO3. (Electrochemically synthesized poly(3,4-ethylenedioxthiophene) has an onset of −0.65 V.)

The monomer, 2-(perfluorobutyl)-thieno[3,4-b]thiophene with a very negative HOMO level can be used as an additive for the overcharge protection in a nonaqueous rechargeable lithium battery. The additive must be capable of undergoing polymerization in order to protect the battery from overcharging. The additive polymerizes at voltages above the maximum permissible cell voltage of the battery during overcharging. Monomers with very negative HOMO levels are ideally suited for this application.

The essential characteristics of the present invention are described completely in the foregoing disclosure. One skilled in the art can understand the invention an make various modifications without departing from the spirit of the invention and without deviating from the scope and equivalents of the following claims.

The invention claimed is:

1. A composition of matter represented by the formula

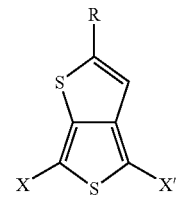

wherein R is a partially or fully fluorinated primary, secondary or tertiary alkyl having from 1 to 8 carbon atoms; and X and X' are independently selected from the group consisting of a polymerizable cyclic pi-conjugated carbon-ring structure optionally comprising S, N or O heteroatoms, and phenyl, naphthyl, pyrryl, dithienyl, thienyl and their respective substituted derivatives.

2. The composition of matter of claim 1 wherein the polymerizable cyclic pi-conjugated carbon-ring structure consists of a pi-conjugated single carbon-ring structure optionally comprising S, N, or O heteroatoms.

3. The composition of matter of claim 1 wherein the polymerizable cyclic pi-conjugated carbon-ring structure consists of a pi-conjugated two or three fused carbon-ring structure optionally comprising S, N or O heteroatoms.

4. The composition of matter of claim 1 wherein at least one of X and X' is selected from the group consisting of phenyl, naphthyl, pyrryl, dithienyl, thienyl and their respective substituted derivatives.

5. The composition of matter of claim 1 wherein at least one of X and X' is thieno[3,4-b]thiophene.

6. The composition of matter of claim 1 wherein at least one of X and X' is thieno[2,3-b]thiophene.

7. The composition of matter of claim 1 which has been treated with a dopant.

8. The composition of matter of claim 1 wherein R is trifluoromethyl, perfluoroethyl, perfluoropropyl, perfluorobutyl, 2,2,2-trifluoromethyl-ethyl and 2,2,2-trifluoro-1,1-bis-trifluoromethyl-ethyl.

9. The composition of matter of claim 1 where in R is perfluorobutyl.

10. The composition of matter of claim 1 further comprising at least one member selected from the consisting of polyacrylic acid, polymethacrylic acid, polymaleic acid, polystyrene sulfonic acid, a perfluorosulfonic acid polymer, polyvinyl sulfonic acid and poly(styrene-co-acrylonitrile) sulfonic acid and mixtures thereof.

11. The composition of matter of claim 1 further comprising ethylenedioxythiophene.

12. The composition of matter of claim 1 further comprising tetrabutylammonium hexafluorophosphate.

* * * * *